United States Patent
Lin et al.

(10) Patent No.: US 10,195,237 B2
(45) Date of Patent: *Feb. 5, 2019

(54) **COMPOSITIONS AND METHODS FOR TREATING INFLAMMATORY RELATED DISEASES OR CONDITIONS USING *PEDIOCOCCUS ACIDILACTICI* PROBIOTICS**

(71) Applicant: IMAGILIN TECHNOLOGY LLC, Frederick, MD (US)

(72) Inventors: Jhy-Jhu Lin, Potomac, MD (US); Jolinta Lin, Baltimore, MD (US)

(73) Assignee: IMAGILIN TECHNOLOGY LLC, Frederick, MD (US)

(*) Notice: Subject to any disclaimer, the term of this patent is extended or adjusted under 35 U.S.C. 154(b) by 42 days.

This patent is subject to a terminal disclaimer.

(21) Appl. No.: 15/072,308

(22) Filed: Mar. 16, 2016

(65) Prior Publication Data

US 2017/0020929 A1   Jan. 26, 2017

Related U.S. Application Data

(60) Provisional application No. 62/386,347, filed on Nov. 30, 2015, provisional application No. 62/177,468, filed on Mar. 16, 2015.

(51) Int. Cl.
| | | |
|---|---|---|
| *A61K 35/744* | (2015.01) | |
| *A61K 31/138* | (2006.01) | |
| *A61K 31/555* | (2006.01) | |
| *A61K 31/704* | (2006.01) | |
| *A61K 38/50* | (2006.01) | |

(52) U.S. Cl.
CPC .......... *A61K 35/744* (2013.01); *A61K 31/138* (2013.01); *A61K 31/555* (2013.01); *A61K 31/704* (2013.01); *A61K 38/50* (2013.01); *C12Y 305/01001* (2013.01)

(58) Field of Classification Search
CPC .. A61K 35/744; A61K 31/138; A61K 31/555; A61K 38/50; A61K 31/704; C12Y 305/01001
See application file for complete search history.

(56) References Cited

U.S. PATENT DOCUMENTS

| | | |
|---|---|---|
| 6,692,779 B2 | 2/2004 | Dominques |
| 7,579,030 B2 | 8/2009 | Domingues |
| 7,935,334 B2 | 5/2011 | Lin |
| 8,318,152 B2 | 11/2012 | Lin |
| 8,496,923 B2 | 7/2013 | Lin |
| 9,289,008 B1 | 3/2016 | Lin |
| 9,364,507 B2 | 6/2016 | Lin |
| 9,789,141 B2 | 10/2017 | Lin |
| 2006/0008511 A1* | 1/2006 | Lin ............. A61K 35/742 424/442 |
| 2009/0263366 A1* | 10/2009 | Lin ............. A61K 35/744 424/93.44 |
| 2010/0094243 A1 | 4/2010 | Wiggins |
| 2013/0064885 A1 | 3/2013 | Lin |
| 2014/0093614 A1 | 4/2014 | Gonzalez |
| 2014/0193464 A1 | 7/2014 | Lin |
| 2015/0246082 A1 | 9/2015 | Lin |
| 2016/0193259 A1 | 7/2016 | Lin |
| 2016/0243173 A1 | 8/2016 | Lin |
| 2017/0143777 A1 | 5/2017 | Lin |

FOREIGN PATENT DOCUMENTS

WO   2017095968 A1   6/2017

OTHER PUBLICATIONS

MitoMax—premium probiotics for dogs and cats. 2017. downloaded from www.amazon.com/MitoMax-premium-probiotics-dogs-capsules-bottle/dp/B003NH02DW. p. 1 (Year: 2017).*
International Search Report from International Appl. No. PCT/US2016/064286 dated Mar. 23, 2017.
U.S. Office Action from U.S. Appl. No. 15/365,916, dated May 15, 2018.
U.S. Office Action from U.S. Appl. No. 13/676,579 dated May 29, 2015.
U.S. Office Action from U.S. Appl. No. 13/676,579 dated Nov. 12, 2015.
Perez et al., Production of four potentially probiotic lactic acid bacteria and their evaluation as feed additives for piglets, Animal Feed Science and Technology, 134:89-107 (2007).
Lin et al., Probiotics as alternative biomedicines for pets with digestive disorders, Proceedings of 8th Annual Meeting of JBVP, p. 288-293 (2006).
Mandal et al., Optimized culture conditions for bacteriocin production by Pediococcus acidilactici LAB 5 and its characterization, Indian Journal of Biochemistry and Biophysics, 45:106-110 (2008).
Furr et al., Orally Administered Pediococcus acidilactici and *Saccharomyces boulardii*—Based Probiotics Alter Select Equine Immune Function Parameters, Journal of Equine Veterinary Science, 34:1156-1163 (2014).

* cited by examiner

*Primary Examiner* — Taeyoon Kim
(74) *Attorney, Agent, or Firm* — Nevrivy Patent Law Group P.L.L.C.

(57) ABSTRACT

The present invention provides a method of treating a disease or condition characterized by inflammation in a subject in need thereof, comprising administering to the subject an effective amount of a *Pediococcus acidilactici* probiotic. Compositions of *Pediococcus acidilactici* probiotic are also provided.

14 Claims, 5 Drawing Sheets

Date

COMPOSITIONS AND METHODS FOR TREATING INFLAMMATORY RELATED DISEASES OR CONDITIONS USING *PEDIOCOCCUS ACIDILACTICI* PROBIOTICS

CROSS REFERENCE TO RELATED APPLICATIONS

This application claims the benefit of U.S. Provisional Appl. No. 62/386,347, filed Nov. 30, 2015 and U.S. Provisional Appl. No. 62/177,468, filed Mar. 16, 2015. The content of the aforesaid applications are relied upon and incorporated by reference in their entirety.

FIELD OF THE INVENTION

The field of the invention relates to compositions and uses of *Pediococcus acidilactici* bacteria.

BACKGROUND OF THE INVENTION

Probiotics are beneficial microorganisms naturally existing in gastrointestinal (GI) tracts of humans and animals. In 2001, the World Health Organization defined probiotics as "Live microorganisms, which, when administered in adequate amounts, confer a health benefit on the host" (Joint FAO/WHO Expert Consultation Report, 2001). Many probiotics-related health benefits such as decreasing symptoms from antibiotics-induced diarrhea, acute diarrhea, traveler diarrhea, allergy, respiratory and urinary tract infections, inflammatory bowel disease, irritable bowel syndrome, colon and bladder cancer, and rheumatoid arthritis have been reported. Conventionally, *Bifidobacterium* and *Lactobacillus* are commercially available probiotics. However, these bacteria are sensitive to air exposure, elevated temperature, and stomach acids.

*Pediococcus acidilactici* is a plant based probiotic that is widely applied in sausage preparation for human consumption and as animal feed additives to improve animal health. Moreover, *P. acidilactici* was reported to be able to stimulate the antibody production against parasitic infection of broiler chicken coccidiosis, and ovalbumin antibody production in ovalbumin vaccinated horses (Furr et al., *Journal of Equine Veterinary Science*, 34:1156-1163 (2014)). Both T-cell and B-cell multiplication were detected in rats fed with *Pediococcus*-based probiotics which were mixtures of *P. acidilactici* and *Saccharomyces boulardii*.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

According to non-limiting example embodiments, in one aspect, the invention provides a method of treating a disease or condition characterized by inflammation in a subject in need thereof, comprising administering to the subject an effective amount of a *Pediococcus acidilactici* probiotic.

In some embodiments, the administration of *Pediococcus acidilactici* probiotic increases the number of anti-inflammatory M2 macrophage cells in the subject, thereby treating the disease or condition. In some embodiments, the administration of *Pediococcus acidilactici* probiotic increases IL-10 production in the subject, thereby treating the disease or condition. In some embodiments, the administration of *Pediococcus acidilactici* probiotic decreases the levels of IL-6 and/or IL-23 in the subject, thereby treating the disease or condition.

In some embodiments, the disease or condition characterized by inflammation is selected from the group consisting of malignancy (cancer), arthritis, cardiovascular disease, hepatitis, infection, wound healing, pancreatitis, gastroesophageal reflux disease, diabetes, inflammatory bowel disease, peptic ulcer disease, bronchitis, cholecystitis, appendicitis, bursitis, dermatitis, asthma, autoimmune disease, pelvic inflammatory disease, gout, trauma, foreign body infection, burns, dental work, tendonitis, rhinitis, mucositis, and exposure to toxins such as chemicals and alcohol.

In some embodiments, the *Pediococcus acidilactici* probiotic is strain NRRL B-50517. In some embodiments, the subject is a human.

In some embodiments, the subject is administered greater than $1.0 \times 10^9$ cfu of the probiotic. In some embodiments, the subject is administered greater than $4.0 \times 10^9$ cfu of the probiotic.

In some embodiments, the subject is administered one or more additional therapeutic agents. In some embodiments, the subject is administered one or more chemotherapeutic (anti-cancer) agents and/or radiotherapy in combination with the *Pediococcus acidilactici* probiotic.

In some embodiments, the subject is not administered another therapeutic agent. In some embodiments, the subject is not administered another probiotic.

In another aspect, the invention provides a composition comprising a *Pediococcus acidilactici* probiotic. In some embodiments, the *Pediococcus acidilactici* is strain NRRL B-50517. In some embodiments, the composition is a pharmaceutical composition.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1:
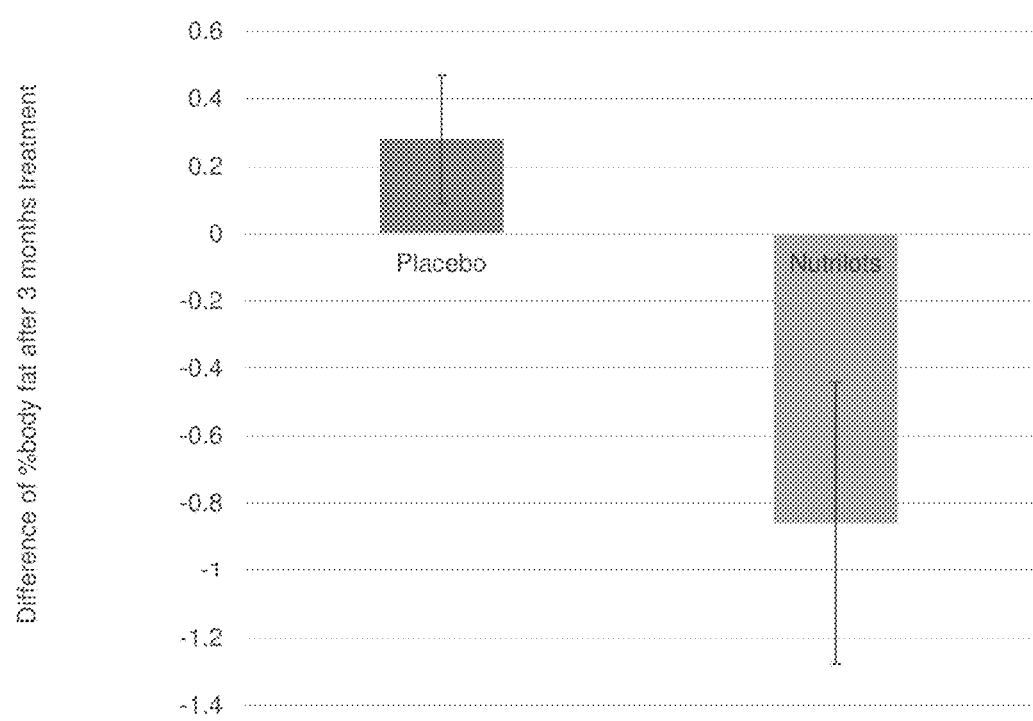
FIG. 1. Effect of *P. acidilactici* 5051 probiotic on body fat %.

The invention is based, in part, on the surprising discovery that administration of effective amounts of a *Pediococcus acidilactici* probiotic are able to treat diseases or conditions characterized by inflammation.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

I. Methods

According to non-limiting example embodiments, in one aspect, the invention provides a method of treating a disease or condition characterized by inflammation in a subject in need thereof, comprising administering to the subject an effective amount of a *Pediococcus acidilactici* probiotic.

As used herein, "treat" and all its forms and tenses (including, for example, treating, treated, and treatment) refers to therapeutic treatment. In certain aspects of the invention, those in need of treatment include those already with a pathological disease or condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the disease or pathological condition.

The subject to be treated herein is not limiting. In some embodiments, the subject to be treated is a mammal, bird, reptile or fish. Mammals that can be treated in accordance with the invention, include, but are not limited to, humans, dogs, cats, horses, mice, rats, guinea pigs, sheep, cows, pigs, monkeys, apes and the like, subject to a disease or other pathological condition characterized by inflammation. The term "patient" and "subject" are used interchangeably. In some embodiments, the subject is a human.

The *Pediococcus acidilactici* probiotic can be administered 1, 2, 3, 4, 5, 6, 7, 8, 9, 10, 11, or 12 times per day. In some embodiments, the *Pediococcus acidilactici* probiotic is administered 4 times a day, 2 times a day, or once per day. In some embodiments, the *Pediococcus acidilactici* probiotic is administered every 2 hours, every 4 hours, every six hours, every 8 hours, every 10 hours, every 12 hours or every 24 hours. In some embodiments, the *Pediococcus acidilactici* probiotic is administered once a day.

The duration of administration of the *Pediococcus acidilactici* probiotic can vary for each individual to be treated/administered depending on the individual cases and the diseases or conditions to be treated. In some embodiments, the *Pediococcus acidilactici* probiotic can be administered continuously for a period of several days, weeks, months, or years of treatment or can be intermittently administered where the individual is administered the *Pediococcus acidilactici* probiotic for a period of time, followed by a period of time where they are not treated, and then a period of time where treatment resumes as needed to treat the disease or condition. For example, in some embodiments, the individual to be treated is administered the *Pediococcus acidilactici* probiotic of the invention daily, every other day, every three days, every four days, 2 days per week 3 days per week, 4 days per week, 5 days per week or 7 days per week. In some embodiments, the individual is administered the *Pediococcus acidilactici* probiotic for 1 week, 2 weeks, 3 weeks, 4 weeks, 1 month, 2 months, 3 months, 4 months, 5 months, 6 months, 7 months, 8 months, 9 months, 10 months, 11 months, 1 year or longer.

In some embodiments, the administration of *Pediococcus acidilactici* probiotic increases the number of anti-inflammatory M2 macrophage cells in the subject, thereby treating the disease or condition. In some embodiments, the anti-inflammatory M2 macrophage cells increase by about 10%, about 20%, about 30%, about 40%, about 50%, about 60%, about 70%, about 80%, about 90%, about 100%, about 125%, about 150%, about 175%, about 200%, about 250%, about 300%, about 350%, about 400%, or about 450%, about 500%, about 600%, about 700%, about 800%, about 900% or about 1000% or more over untreated levels.

In some embodiments, the administration of *Pediococcus acidilactici* probiotic increases IL-10 production in the subject, thereby treating the disease or condition. In some embodiments, the IL-10 production increases by about 10%, about 20%, about 30%, about 40%, about 50%, about 60%, about 70%, about 80%, about 90%, about 100%, about 125%, about 150%, about 175%, about 200%, about 250%, about 300%, about 350%, about 400%, or about 450%, about 500%, about 600%, about 700%, about 800%, about 900% or about 1000% or more over untreated levels.

In some embodiments, the administration of *Pediococcus acidilactici* probiotic decreases the levels of IL-6 and/or IL-23 in the subject, thereby treating the disease or condition. In some embodiments, the levels of IL-6 and/or IL-23 decrease by about 10%, about 20%, about 30%, about 40%, about 50%, about 60%, about 70%, about 80%, about 90%, or about 100% over untreated levels.

In some embodiments, the administration of *Pediococcus acidilactici* probiotic increases the number of anti-inflammatory M2 macrophage cells in the subject, in combination with increasing IL-10 production, and optionally decreasing IL-6 and/or IL-23 in the subject.

In some embodiments, the disease or condition characterized by inflammation is selected from the group consisting of malignancy (cancer), arthritis, cardiovascular disease, hepatitis, infection, wound healing, pancreatitis, gastroesophageal reflux disease, diabetes, inflammatory bowel disease, peptic ulcer disease, bronchitis, cholecystitis, appendicitis, bursitis, dermatitis, asthma, autoimmune disease, pelvic inflammatory disease, gout, trauma, foreign body infection, burns, dental work, tendonitis, rhinitis, mucositis, and exposure to toxins such as chemicals and alcohol.

As used herein, "cancer" refers to a pathophysiological condition whereby cells are characterized by dysregulated and/or proliferative cellular growth and the ability to induce said growth, which includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, meduUoblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, meduUoblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplasia syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenstrom's macroglobulinemia, Wilms' Tumor, and women's cancers.

The *Pediococcus acidilactici* probiotic that can be used in accordance with the invention is not limiting. In some embodiments, the *Pediococcus acidilactici* is a strain that is viable above 65° C., is able to grow in aerobic and anaerobic conditions, and in a pH range between 1 and 6.2. In some embodiments, the *Pediococcus acidilactici* is a strain deposited in the Agricultural Research Service (ARS) Patent Culture Collection as NRRL B-50517. Strain NRRL B-50517 is described in U.S. application Ser. No. 13/676,579, which is herein incorporated by reference.

In some embodiments, the *Pediococcus acidilactici* for use in the invention can be selected for tolerance to elevated temperatures, low pH values, and aerobic and anaerobic conditions.

In accordance with the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition. In some embodiments, the subject is administered greater than $1.0 \times 10^9$ cfu of the probiotic. In some embodiments, the subject is administered greater than $4.0 \times 10^9$ cfu of the probiotic.

In some embodiments, the subject is administered one or more additional therapeutic agents. In some embodiments, the one or more additional therapeutic agents are those commonly used to treat the disease or condition characterized by inflammation.

In some embodiments, the subject is administered in combination an anti-inflammatory drug. In some embodiments, the administered *Pediococcus acidilactici* and anti-inflammatory drug act synergistically. In some embodiments, the anti-inflammatory drug is a non-steroidal anti-inflammatory drug (NSAID). In some embodiments, anti-inflammatory drug is selected from the group consisting of Antazoline, Balsalazide, Beclometasone, Betamethasone, Budesonide, Celecoxib, Colchicine, Deflazacort, Dexamethasone, Dexibuprofen, Diclofenac, Etanercept, Etodolac, Felbinac, Fenoprofen, Flumetasone, Fluorometholone, Flurbiprofen, Flurbiprofen, Fluticasone, Gentamicin, Hydrocortisone, Ibuprofen, Indometacin, Ketoprofen, Loteprednol, Mefenamic acid, Meloxicam, Mesalazine, Methylprednisolone, Mometasone, Nabumetone, Naproxen, Nepafenac, Olsalazine, Prednisolone, Rimexolone, Sulfasalazine, Sulindac, Tenoxicam, Tiaprofenic acid, Triamcinolone and combinations thereof.

In some embodiments, the subject is administered one or more anti-cancer agents and/or radiotherapy in combination with the *Pediococcus acidilactici* probiotic to treat cancer in the subject.

In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Margibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Di sodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perj eta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide.

In some embodiments, the subject is not administered another therapeutic agent and is administered a composition consisting of or consisting essentially of the *Pediococcus acidilactici* probiotic.

In some embodiments, the subject is administered one or more additional probiotics. In some embodiments, the subject is not administered another probiotic.

II. Compositions

In some embodiments, the invention provides a composition comprising a *Pediococcus acidilactici* probiotic. In some embodiments, the composition comprises *Pediococcus acidilactici* NRRL B-50517. In some embodiments, the compositions comprise effective amounts of *Pediococcus acidilactici*, including *Pediococcus acidilactici* NRRL B-50517.

In some embodiments the compositions are pharmaceutical compositions. In some embodiments, the compositions are pharmaceutical compositions comprising effective amounts of *Pediococcus acidilactici*, including *Pediococcus acidilactici* NRRL B-50517 which are capable of treating of one or more diseases or conditions characterized by inflammation.

In some embodiments, the pharmaceutical composition comprises one or more pharmaceutically acceptable carriers or excipients. Pharmaceutically acceptable carriers and excipients are those that are compatible with the other ingredients in the formulation and biologically acceptable. The *Pediococcus acidilactici* can be provided in combination with a pharmaceutically acceptable carrier, excipients or diluent. Suitable carriers, excipients and/or diluents include, but are not limited to, pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The *Pediococcus acidilactici* can also be administered in sachets that have to be added to a glass of water and then drunk.

In some embodiments, the composition is suitable for oral administration. In some embodiments, the composition is a tablet, capsule, pill, dragee, suspension, lozenge, emulsion, aqueous solution, liquid, gel, or syrup. In some embodiments, the compositions can be delivered in the form of functional foods and/or beverages, as well as in the form of various supplements.

Formulations of the present invention suitable for oral administration may be presented as discrete units such as capsules, cachets or tablets each containing a predetermined amount of the *Pediococcus acidilactici*; as a powder or granules, which in some embodiments can be wettable, spray-dried or freeze-dried; as a solution or a suspension in an aqueous or non-aqueous liquid; or as an oil-in-water liquid emulsion or a water-in-oil liquid emulsion.

In some embodiments, a tablet can be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

In some embodiments, the composition comprises one or more of the following: tablets, pills, capsules, ovules, solutions or suspensions, which may contain flavouring or colouring agents, for immediate-, delayed-, modified-, sustained-, pulsed- or controlled-release applications.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

In some embodiments, the compositions of the invention are formulated in unit dosage form for ease of administration and uniformity of dosage. The term "unit dosage form" as used herein refers to physically discrete units suited as unitary dosages for the individuals to be treated. In some embodiments, the compositions are formulated into discrete dosage units each containing a predetermined "unit dosage" or "unit dose" of one or more active compounds calculated to produce the desired effect in association with the required pharmaceutical carrier.

In some embodiments, the composition comprises gelatin capsules. In some embodiments, the gelatin capsules comprise effective amounts of *P. acidilactici* NRRL B-50517 fermentative cultures with peach fruit powder, in a dose of from about 1-4 billion CFU.

While is it possible to administer *Pediococcus acidilactici* alone according to the present invention, the *Pediococcus acidilactici* are typically administered on or in a support as part of a product, in particular as a component of a food product, a dietary supplement or a pharmaceutical formulation. These products typically contain additional components well known to those skilled in the art.

In one embodiment, the *Pediococcus acidilactici* are employed according to the invention in a food product such as a food supplement, a drink or a powder based on milk. Here, the term "food" is used in a broad sense—and covers food for humans as well as food for animals (i.e. a feed). In one embodiment, the food is for human consumption.

The food may be in the form of a solution or as a solid—depending on the use and/or the mode of application and/or the mode of administration.

When used as, or in the preparation of, a food, such as functional food, the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice or a beverage comprising whey protein, health teas, cocoa drinks, milk drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

In some embodiments, the food product employed according to the invention is a fermented milk or humanized milk.

In some embodiments, the compositions can be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

In some embodiments, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a viable microorganism.

In some embodiments, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

In some aspects, the microorganisms according to the present invention are used as, or in the preparation of, animal feeds, such as livestock feeds, in particular poultry (such as chicken) feed, pet food, or pet treats.

In some embodiments, where the product is a food product, the *Pediococcus acidilactici* should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognize that shelf-life times will vary upon the type of foodstuff, the size of the foodstuff, storage temperatures, processing conditions, packaging material and packaging equipment.

In some embodiments, the composition of the present invention may be used as a food ingredient and/or feed ingredient. As used herein the term "food ingredient" or "feed ingredient" includes a formulation which is or can be added to functional foods or foodstuffs as a nutritional supplement. The food ingredient may be in the form of a solution or as a solid—depending on the use and/or the mode of application and/or the mode of administration.

In some embodiments, the composition of the present invention may be—or may be added to—food supplements (also referred to herein as dietary supplements).

In some embodiments, the composition of the present invention may be—or may be added to—functional foods. As used herein, the term "functional food" means food which is capable of providing not only a nutritional effect, but is also capable of delivering a further beneficial effect to consumer. Accordingly, functional foods are ordinary foods that have components or ingredients (such as those described herein) incorporated into them that impart to the food a specific functional—e.g. medical or physiological benefit—other than a purely nutritional effect. Although there is no legal definition of a functional food, most of the parties with an interest in this area agree that they are foods marketed as having specific health effects beyond basic nutritional effects. Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

The present invention is further illustrated by the following Examples. These Examples are provided to aid in the understanding of the invention and are not to be construed as a limitation thereof.

EXAMPLES

Example 1—*P. Acidilactici* Administration Stimulates Innate Immune Responses in Animals This example describes the effect of administering *P. acidilactici* on innate immune responses in rats.

TABLE 1

Stimulation of macrophage activities on rats fed with *Pediococcus*-based probiotics

|  | MAC* |
|---|---|
| Control | 4.0 ± 0.3 |
| Low | 4.0 ± 0.5 |
| Medium | 6.0 ± 1.6 |
| High | 7.2 ± 1.5 |

*Sprague Dawley rats (9 weeks) were fed Harlan #7012 rat chow ad libitum. The probiotic was *Pediococcus*-based probiotics (Imagilin, Frederick, MD). There were four groups (n = 10): control group (no probiotic); low dose ($1 \times 10^9$ cfu); mid group dose ($2 \times 10^9$); and high dose ($10 \times 10^9$). Animals were given 2 grams of food mixed with probiotic at 11 a.m. Then from 8 pm to 11 am, chow supplied ad libitum. Water was ad libitum 24 h. Tail blood samples were analyzed for complete blood counts.

When the rats were administered $2.0 \times 10^9$ to $10 \times 10^9$ cfu *Pediococcus*-based probiotics per day for 15 days, the amounts of macrophages increased 150% to 180% comparing to those from rats without probiotics. The increase of macrophages indicates that *Pediococcus*-based probiotics can stimulate rat innate immune responses. Interestingly, when rats were fed with low amounts ($1.0 \times 10^9$) of *Pediococcus*-based probiotics, the number of macrophages were similar to the amounts of macrophages as those from the control. This indicates that adequate amounts of *Pediococcus*-based probiotics are required to stimulate innate immune responses, such as increasing the amounts of macrophage cells.

Example 2—*P. acidilactici* Administration Stimulates Cytokine Production in Human Subjects This example describes the effect of administering *P. acidilactici* on cytokine production in human subjects.

For innate immune responses, macrophages are broadly divisible into two groups: pro-inflammatory M1 macrophages and anti-inflammatory M2 macrophages. The M2 macrophages also refers to macrophages that function in constructive processes like wound healing and tissue repair, and those that turn off damaging immune system activation by producing anti-inflammatory cytokines like interleukin-10 (IL-10).

TABLE 2

Increase of interleukin-10 (IL-10) on *Pediococcus* probiotics treated human volunteer subjects.

| | Detection of IL-6 | | | Detection of IL-10 | | |
|---|---|---|---|---|---|---|
| Participant ID | Before treated *Pediococcus* probiotics | After treated *Pediococcus* probiotics | % of IL-6 after treated *Pediococcus* probiotics | Before treated *Pediococcus* probiotics | After treated *Pediococcus* probiotics for 45 days | % of IL-10 after treated *Pediococcus* probiotics |
| AB01 | 0.50 | 0.29 | 58% | 1.99 | 3.99 | 200% |
| AB02 | 1.77 | 0.93 | 53% | 4.44 | 8.16 | 183% |
| AB03 | 1.94 | 1.72 | 89% | 5.66 | 8.95 | 158% |

TABLE 2-continued

Increase of interleukin-10 (IL-10) on *Pediococcus* probiotics treated human volunteer subjects.

| | Detection of IL-6 | | | Detection of IL-10 | | |
|---|---|---|---|---|---|---|
| Participant ID | Before treated *Pediococcus* probiotics | After treated *Pediococcus* probiotics | % of IL-6 after treated *Pediococcus* probiotics | Before treated *Pediococcus* probiotics | After treated *Pediococcus* probiotics for 45 days | % of IL-10 after treated *Pediococcus* probiotics |
| AB04 | 0.72 | 0.93 | 129% | 4.44 | 8.79 | 198% |
| AB05 | 0.12 | 0.19 | 158% | 0.77 | 3.25 | 422% |
| | | | 97.4% Average | | | 232% Average |

*: Serum samples were collected from five volunteers before administration of *Pediococcus acidilactici* NRRL B-50517 probiotics, and after administration of 4 billion cfu of *Pediococcus* probiotics per day for 45 days. Serum samples were analyzed using Luminex-based multiplex assays (EMD Millipore; Milliplex) designed to measure biomarkers associated with pro-inflammatory IL-6 and anti-inflammatory IL-10.

All five volunteers exhibited significantly increased anti-inflammatory IL-10 activity (from 158% to a 422% increase) after administration of *Pediococcus* probiotics for 45 days. On the contrary, the effect on pro-inflammatory IL-6 showed inconsistent results, which exhibited decreased activity in three volunteers and increased activity in two volunteers. These results demonstrate that administration of *Pediococcus* probiotics in human subjects may enhance more than two fold the anti-inflammatory IL-10 activity. These results, together with the results showing increases of macrophages in *Pediococcus*-based probiotics treated rats indicate that *Pediococcus*-based probiotics can enhance innate immunity of humans and animals. The innate immune responses of humans and animals treated with *Pediococcus* exhibit increases of M2 macrophage and anti-inflammatory IL-10.

Example 3—Effects of *P. acidilactici* NRRL B-50517 Supplementation for Use in Weight Management: A Controlled, Randomized, Double-Blind Trial This weight management study assessed the effect of a 12 week supplementation of *Pediococcus acidilactici* NRRL B-50517 probiotic strain on 30 adult participants in a controlled, randomized, double blind trial. Percent body fat was measured at the beginning and end of the trial with bioelectric impedance analysis (BIA). Levels of proinflammatory biomarkers interleukin-6 (IL-6) and interleukin-23 (IL-23) were determined using blood samples collected before the trial began and after it concluded. Appetite, energy level, bowel movement, stool quality, bloating, and gas, were monitored throughout the study using weekly questionnaires. The specific weight loss and anti-inflammatory effect of *P. acidilactici* is described here for the first time. Daily supplementation with 4 billion CFU *P. acidilactici* resulted in on average, the probiotic group lost 0.86±0.42% percent body fat whereas the control group gained 0.28%±0.19, p=0.0264. Pro-inflammatory IL-6 ratios differed by 0.61±0.22 and 3.06±0.87 in probiotic and control groups, respectively (p=0.0295); pro-inflammatory IL-23 ratio was 0.65±0.14 in the probiotic and 1.71±0.38 in the control groups, p=0.0068.

Methods and Materials

Participants in the study were selected on a volunteer basis; distribution of age, sex, and BMI was equal across treatment groups. Volunteers were not instructed to alter their regular dietary patterns or exercise routines during the study. The probiotic was tested in a group of subjects divided as such: 20% normal weight status (18.5-24.99), 47% overweight (25-29.99), and 33% obese (>30).

Prior to the beginning of the supplementation period, participants underwent an extensive physical exam including a bioelectric impedance analysis to determine body fat percentage and blood work to quantify IL-6 and IL-23 levels. The same exam procedure was repeated at the conclusion of the study. Over the course of 12 weeks, 30 participants were administered either 2 gelatin capsules containing a compound of *P. acidilactici* NRRL B-50517 fermentative cultures with peach fruit powders once daily, amounting to a dose of 4 billion CFU *Pediococcus* probiotics/day, or a placebo treatment of 2 capsules containing only peach powder. The safety of the probiotic was analyzed in terms of impact on appetite, energy level, bowel movement, stool quality, bloating, and gas. As part of a weekly questionnaire, participants were asked to score their experience of these symptoms on an arbitrary scale from 1 to 5, 1 being the least severe and 5 being the most severe.

Results

Figure 2:
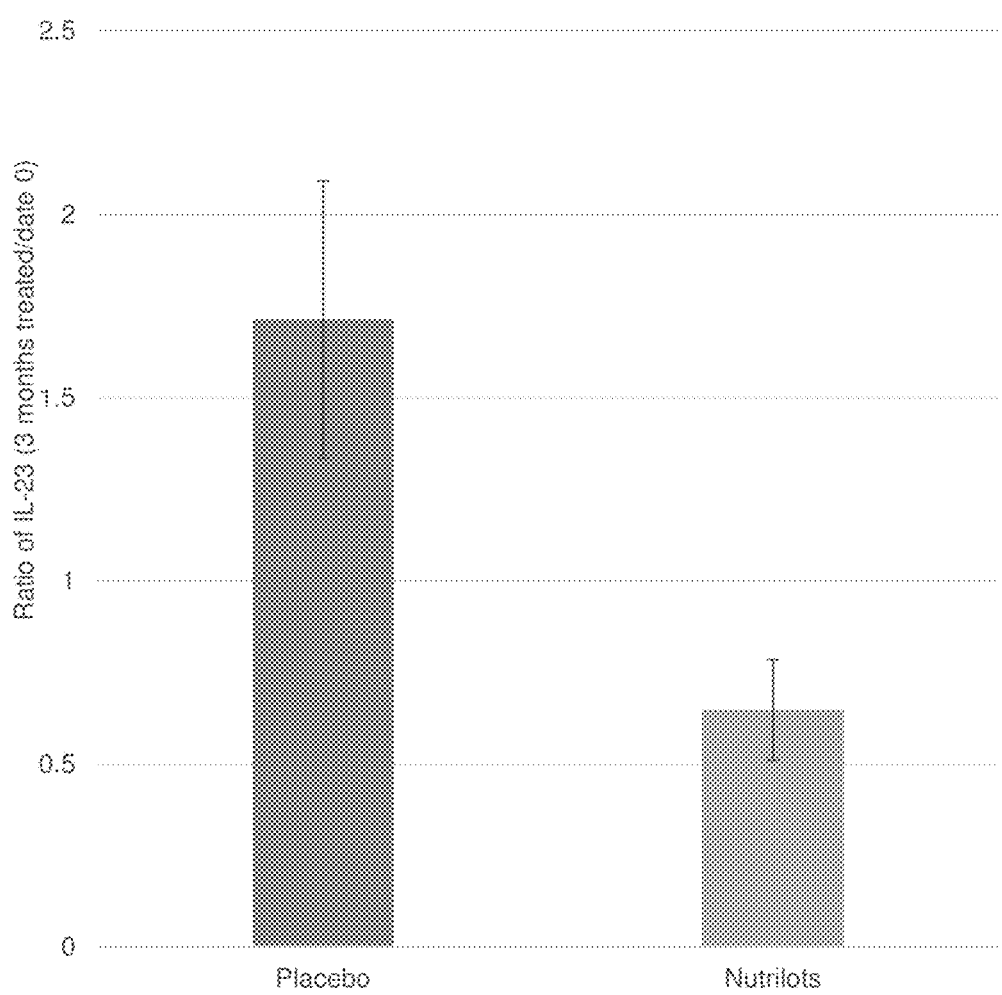
FIG. 2. Effect of *P. acidilactici* 5051 probiotic on IL-23 activity.
Figure 3:
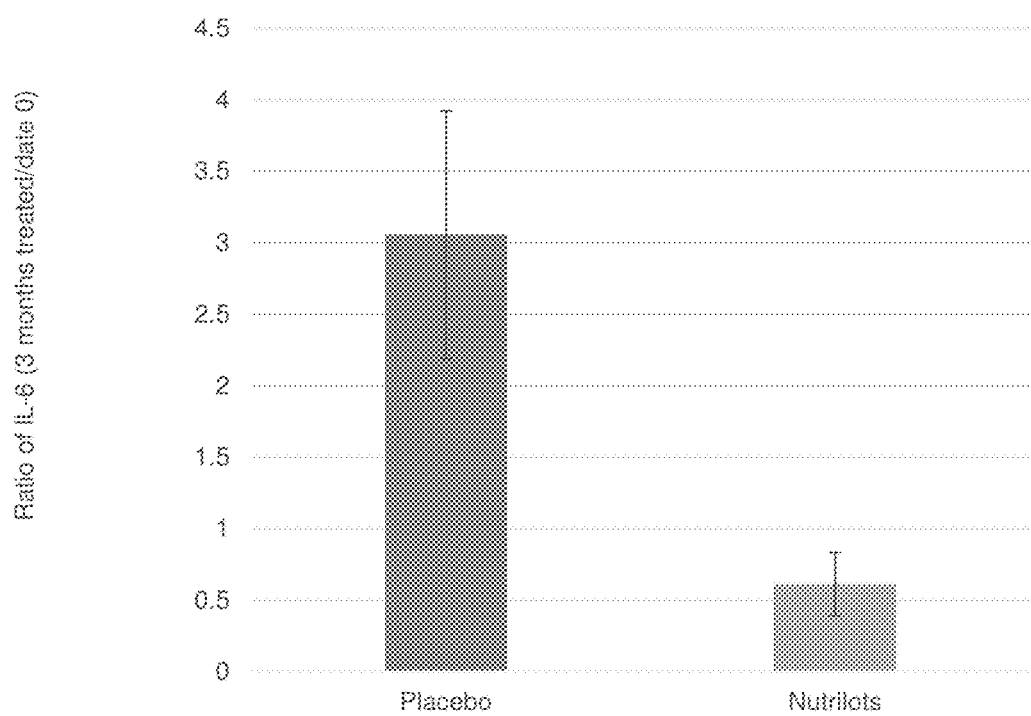
FIG. 3. Effect of *P. acidilactici* 5051 probiotic on IL-6 activity.

The present results show for the first time that supplementation of the probiotic *Pediococcus acidilactici* NRRL B-50517 to the diet of overweight and obese individuals alters bodily fat storage and influences concentration of inflammatory biomarkers linked to the pathology of obesity. The clear difference between % body fat, IL-6 and IL-23 levels observed between placebo and 5051-treated groups at the conclusion of the study demonstrate the effect of the probiotic to support weight loss even without traditional dietary modification or exercise. Results are shown in FIGS. 1-3. Error bars for all three graphs reflect that the respective values of percent body fat, IL-6, and IL-23 for the placebo and probiotic treated groups are not within one standard deviation of one another and thus signal a significant difference between the two.

Shown in FIG. 1 is the effect of *P. acidilactici* 5051 probiotic on body fat %. Participants were administered either 2 gelatin capsules containing a compound of *P. acidilactici* NRRL B-50517 fermentative cultures with peach fruit powders once daily, amounting to a dose of 4 billion CFU *Pediococcus* probiotics/day, or 2 capsules containing only peach powder. % body fat was determined by bioelectric impedance analysis (BIA) test. Values are based on double blind field evaluations of *Pediococcus* probiotics on total 30 volunteers for 3 months treatment. P=0.0264, t=2.4073, placebo mean=0.280±0.190 (SEM); NutriLots™ mean=−0.864±0.418 (SEM). The significantly higher difference in percent body fat observed in the probiotic-treated group (NutriLots) as compared to the placebo group after 3 months of treatment supports that *P. acidilactici* NRRL B-50517 supplementation can result in accelerated weight loss with no changes to diet or exercise patterns.

Impact of *Pediococcus*-Probiotic Supplementation on Inflammatory Biomarkers IL-6 and IL-23.

Shown in FIG. 2 is the effect of *P. acidilactici* 5051 probiotic on IL-23. Blood samples were collected from each participant either with placebo or with probiotics before the study began and after the treatment period concluded to determine changes in IL-6 and IL-23 presence. Marked decreases in both IL-6 and IL-23 were observed in the *Pediococcus*-probiotic treated group. Values are based on double blind field evaluations of *Pediococcus* probiotics on total 30 volunteers for 3 months treatment. P=0.0295, t=2.4239, placebo mean=3.058±0.867 (SEM); NutriLots™ mean=−0.612±0.221 (SEM). The lower ratio of IL-23 in the probiotic-treated group (NutriLots) suggests that 5051 is capable of reducing obesity-related inflammation.

Shown in FIG. 3 is the effect of *P. acidilactici* 5051 Probiotic on IL-6. Values are based on double blind field evaluations of *Pediococcus* probiotics on total volunteers for 3 months treatment. P=0.0068, t=3.0194, placebo mean=1.714±0.377 (SEM); NutriLots™ mean= −0.648±0.137 (SEM). The decreased ratio of IL-6 in the probiotic treated group (NutriLots) indicates that 5051 is capable of reducing obesity-related inflammation.

Discussion

In the present study, the 12-week *P. acidilactici* NRRL B-50517 probiotic treatment produced significant decreases in body fat percent, interleukins 6 and 23 when administered to participants of varying BMI (FIGS. 1, 2, and 3). Consistent results across the board indicate that the means of *P. acidilactici* action is not limited exclusively to individuals of obese weight status, but for those who are of lower BMI as well. A majority of previous studies have demonstrated the efficacy of LAB probiotic treatment on solely obese subjects. Where other probiotic strains were ineffective in reducing in the presence of obesity-related inflammation, 5051 decreased levels of both interleukins 6 and 23 as compared to the placebo group.

Safety of the probiotic was confirmed in a separately published study conducted alongside the present research. No significant difference in participant scores of appetite, bowel movement, bloating, stool quality, energy level, or gas was observed between the beginning and conclusion of the trial period in either the placebo or probiotic-treated group.

These findings have tremendous implications for future treatment and prevention of metabolic disease. As a large percentage of the cases of chronic conditions such as cardiovascular disease (CVD) and type 2 diabetes are developed in tandem with obesity, improving the management of this one disease has the potential to considerably reduce the incidence of several other prominent threats to public health.

While previously thought to only act as storage vessels for excess calories in the form of triglycerides, adipocytes have been discovered to play a complex role in metabolism, immunity, and cancer (Calabro P, Yeh E T H. 2007. Obesity, Inflammation, and Vascular Disease: the role of the adipose tissue as an endocrine organ. Subcellular Biochemistry. 42:63-91). White adipose cells secrete proteins including cytokines and hormone-like factors such as adiponectin, leptin, and resistin; this phenomenon is of particular interest because of the involvement of these molecules in vascular and metabolic complications (Calabro P, Yeh E T H. 2007. Obesity, Inflammation, and Vascular Disease: the role of the adipose tissue as an endocrine organ. Subcellular Biochemistry. 42:63-91). In a majority of obese patients, low grade inflammation of white adipose tissue (WAT) resulting from chronic activation of innate immunity poses an increased possibility of insulin resistance, impaired glucose tolerance, and eventual development of diabetic tendencies (Bastard J P, Maachi M, Lagathu C, Kim M J, Caron M, Vidal H, Capeau J, Feve B. 2006. Recent advances in the relationship between obesity, inflammation, and insulin resistance. Eur. Cyt. Net. 17(1): 4-12). Macrophage infiltration of obese WAT acts as a source of pro-inflammatory cytokines, further contributing to the pathogenesis of insulin resistance. Meanwhile, circulating levels of adiponectin, an insulin-sensing effector highly expressed in WAT, are lower in obese than normal weight subjects. The WAT in these individuals overproduces and secretes increased levels of numerous inflammatory molecules including IL-6, another modulator of insulin sensitivity. Thus, the pro-inflammatory pathogenesis of obesity and systemic development of insulin resistance are closely entwined, linked by the modulation of WAT.

Regulation of calorie extraction from dietary substances could be considered a possible mechanism of probiotic action for the results shown here. The composition of human gut microbiota has been consistently implicated as a determinant of body weight as a result of its critical role in nutrient acquisition and energy harvest and regulation (Tennyson C A, Friedman G. 2008. Microecology, obesity, and probiotics. Curr. Opin. Endocr. Diab. Obes. 15(5):422-7; DiBaise J K, Zhang H, Crowell M D, Krajmalnik-Brown R, Decker G A, Rittmann B E. 2008. Gut microbiota and its possible relationship with obesity. Mayo Clinic Proceedings. 83(4):460-69.). There is reason to believe that targeted microbial community moderation through the introduction of a probiotic could then have potential as a novel therapeutic agent in the treatment of metabolic disease. Conscious editing of the microbiome may be the key to reconcile the imbalance between energy intake and expenditure attributed to the obese state.

Unchanged reported scores for appetite in both the placebo and probiotic-treated groups indicate no potential alterations in dietary patterns or influence on satiety hormone leptin.

In decreasing body fat percent while simultaneously lowering serum IL-6 concentration, it can be presumed that *P. acidilactici* 5051 may increase insulin sensitivity and decrease overall systemic inflammation, therefore contributing to lowered risk of type 2 diabetes. As IL-6 is also linked to vascular damage in obese individuals, a lowered serum level of the cytokine would be likely to reduce risk of CVD (Calabro P, Yeh E T H. 2007. Obesity, Inflammation, and Vascular Disease: the role of the adipose tissue as an endocrine organ. Subcellular Biochemistry. 42:63-91). Inflammatory activity in obese individuals, increasing in accordance with WAT macrophage infiltration, can be assumed to decrease upon a loss in body fat.

The results shown here mirror those observed in an analysis of post-surgical results in morbidly obese individuals. Following bariatric surgery, patients have shown clinically relevant decreases in IL-6, triglycerides, cholesterol, LDL, glucose, and insulin correlated to BMI, validating the existence of a relationship between weight and the inflammatory profile, and further elucidating that between BMI and biochemical parameters of chronic metabolic and vascular conditions (Illan-Gomez F, Gonzalvez-Ortega M, Orea-Soler I, Alcaraz-Tafalla M S, Aragon-Alonso A, Pascual-Diaz M, Perez-Paredes M, Lozano-Almela M L. 2012. Obesity and inflammation: change in C-reactive protein, tumor necrosis factor-alpha and interleukin-6 after bariatric surgery. Obes. Surg. 22:950-55).

The marked decrease in IL-23 concentration observed in the probiotic-treated group is also a powerful signifier of lowered disease risk. IL-23/IL-17 is strongly associated with activation of signal pathways leading to tumor formation and the pathway for carcinogenesis. Because stimulation of the IL-23/IL-17 axis has been observed in obese women independent of increases in abdominal fat, insulin resistance, leptin, or MIF levels, it is reasonable to assume that dietary and behavioral patterns associated with the development of obesity, and not the obese state itself, may be responsible (Sumarac-Dumanovic M, Stevanovic D, Ljubic A, Jorga J, Simic M, Stamenkovic-Pejkovic D, Starcevic V, Trajkovic V, Micic D. 2009. Increased activity of interleukin-23/interleukin-17 proinflammatory axis in obese women. Int. J. Obes. 33:151-56).

Conclusions

In summary, the probiotic *P. acidilactici* NRRL B-50517 showed lowering effects on body fat percent, IL-6, and IL-23, suggesting its beneficial influence on weight management and metabolic disease. In light of the evidence set forth in this study, *Pediococcus acidilactici* NRRL B-50517 could prove to be effective in reduction of body fat and inflammation among those individuals seeking to lose weight.

Figure 4:
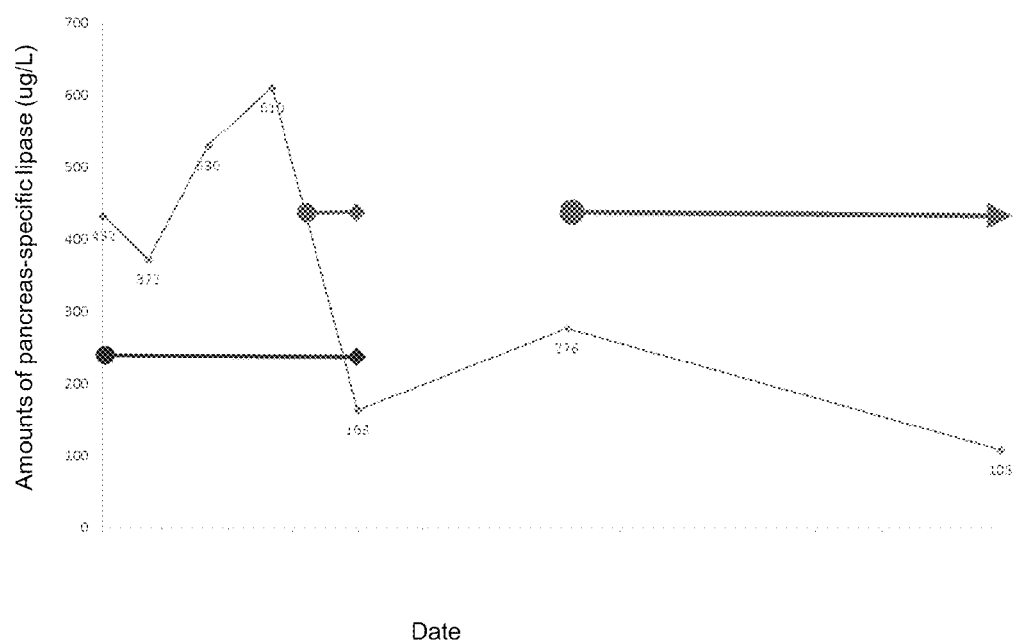
FIG. 4. Effects of *Pediococcus*-based probiotics on a dog with pancreatitis. A 14 years old, female, spayed toy poodle with pancreatitis was treated 100 mg KAMOSTAAL100 twice a day at a point in time (red dot), and the treatment was stopped about 2½ months later (red square). *Pediococcus*-based probiotics were applied (green dot), and stopped at about a month later (green square). After the relapse, *Pediococcus*-based probiotics were applied again (green circle), and continued for a period of time (green arrow).
Figure 5:
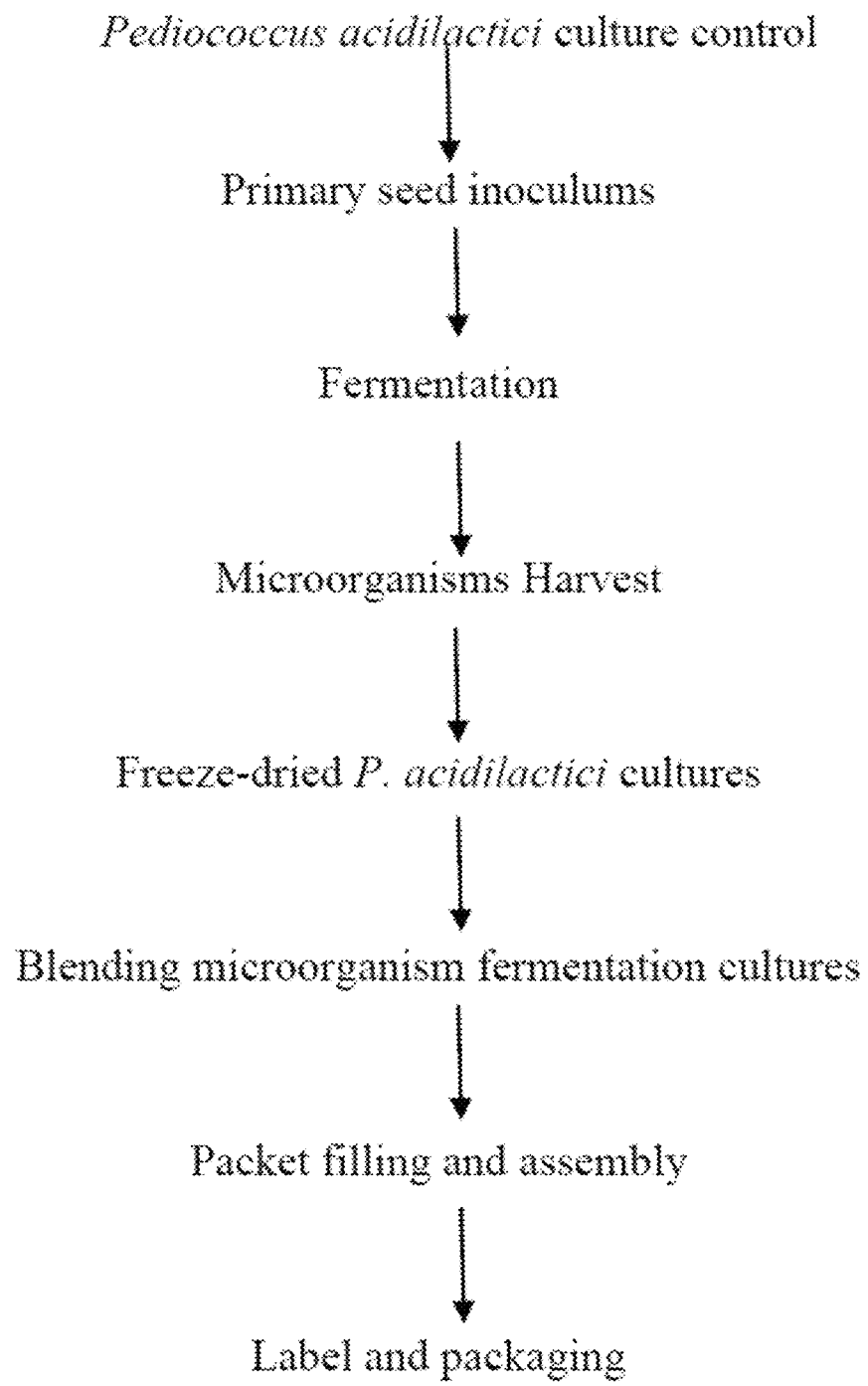
FIG. 5. *Pediococcus acidilactici* NRRL B-50517 manufacture process summary flow chart.

Example 4—Effects of *Pediococcus* Based Probiotics on Dogs and Cats with Pancreatitis A 14 years old, female, spayed toy poodle with significant abdominal pain, vomiting and drop in appetite was diagnosed to possibly suffer from pancreatitis. The images of the ultrasound were shown to have high fats echo from the stomach to the duodenum, and the results of the serum analysis were shown to have spec cPL (Specific Canine Pancreatic Lipase) of 432 ug/L. Although the dog was switched to a low fat diet and treated 100 mg KAMOSTAAL100 twice a day immediately, the spec cPL remained high above 400 and reach 610 ug/L about 2.5 months thereafter with diarrhea and vomiting. At that point, the dog was treated twice a day of 200 mg *Pediococcus*-based probiotics together with current treatment of low fat diet and twice a day 100 mg KAMOSTAAL100. Interestingly, not only diarrhea and vomiting were stopped, the spec cPL was back to normal at 163 ug/L within about 6 weeks. Therefore the treatment of both *Pediococcus*-based probiotics and KAMOSTAAL100 was stopped. However, about three months later, the dog had a relapse with the spec cPL increased to 276 ug/L. At this time, the dog was treated was *Pediococcus*-based probiotics 200 mg twice a day only. The treatment was continued for about 7 months with good control of diarrhea, vomiting, and loss of appetite, and the spec cPL was shown to be normal at 108 ug/L (FIG. 4).

The spec cPL (Specific Canine Pancreatic Lipase) and the spec fPL (Specific Feline Pancreatic Lipase) are the normal spec cPL of canine and are the well-established assays for pancreatitis in dogs and cats. In healthy dogs and cats, the spec cPL is <200 ug/L, and the spec fPL is 0.7-3.5 ug/L. Dogs and cats are regarded to have pancreatitis, when spec cPL is greater than 400 ug/L and the cat spec fPL is >5.4 ug/L. Based on this criteria, we applied *Pediococcus*-based probiotics on two dogs and one cat, of which both dogs had spec cPL>600 ug/L, and the cat had spec fPL 50 ug/L, suffering from pancreatitis. All of these dogs and cats, not only the vomiting and diarrhea were stopped but also the spec cPL and spec fPL were controlled and returned to normal. Moreover, two dogs with possible pancreatitis were also treated, since they had elevated spec cPL (303 ug/L and 205 ug/L).

Example 5—Effects of *Pediococcus* Based Probiotics on the Dogs with Cancers Under Chemotherapy Treatment Four dogs having various cancers and that were undergoing chemotherapy were treated with doses of *Pediococcus* probiotics. After a short period of treatment with the *Pediococcus* probiotics, the dogs experienced improved symptoms.

| Age | Body weight (kg) | Sex | Cancer | Drugs for chemotherapy | Side effects before treatment | Dose of *Pediococcus* | Days of treatment | Improvement |
|---|---|---|---|---|---|---|---|---|
| 16 | 6 | Spayed | Breast cancer - surgery 3rd time | panriifu (anti-breast cancer drug:Tamoxifen) | Diarrhea, lost appetite | 2 billion cfu/day | 3 days | After administered *Pediococcus* based probiotics with anti-cancer drug for 3 days, vomiting stopped, lost appetite recovered. |
| 5 | 16.2 | Castrated | lymphoma | Adriamycin | General clinical condition is good | 4 billion cfu/day | 7 days | Good |
| 12 | 15.7 | Castrated | anal cystoma | Carboplatin | Soft stool | 4 billion cfu/day | 3 days | Good |
| 10 | 35 | female | lymphoma | L-asparaginase (Leunase), | vomiting, diarrhea | 8 billion cfu/day | 4 days | Good after 4 days of treatment, |

-continued

| Age | Body weight (kg) | Sex | Cancer | Drugs for chemotherapy | Side effects before treatment | Dose of Pediococcus | Days of treatment | Improvement |
|---|---|---|---|---|---|---|---|---|
|  |  |  |  | Chlorambucil, Prednisolone, Ulcerlmin (Sucralfate hydrate) |  |  |  | diarrhea recovered |

\*: The chemotherapy treatment and Pediococcus based probiotics administration treatment were performed at Daktari Animal Hospital Central, Torri, and Yaizu.

Example 6—Manufacture of *Pediococcus acidilactici* NRRL B-50517

First the strain needed for the fermentation process is selected from the bacteria being cryoed at −70° C. freezer. Grow the culture in sterile media bottles. When grown, pull samples to verify cleanliness and basic phenotypical purity. If determined to be clean and the cells match initial gram stain smears, approval to make the media (fermentation broth) for the tanks is given. Prior to inoculation, the inoculum tank is CIP'd (Clean In Place) with caustic and acid solutions. We sanitize the tanks prior to filling them with the broth fermentation ingredients which are dumped, mixed, and sterilized. The tank media is sterilized at 220° F.-250° F. for thirty minutes to an hour and a half depending on the volume of the tank. We then bring down the temperature to 85-95° F. to seed the tank with the inoculum. When the inoculation tank is grown, we cool the tank to 55-65° F. When cool, a sample is taken for repeated purity checks. If approved for release then, we repeat the steps for tank preparation and inoculation. Production will inoculate the tanks with the grown and approved inoculum bottles. After all the desired tanks are grown, we repeat the purity checks prior to prepping the centrifuge and concentrating the cells into a condensed liquid. The condensed liquid culture is put into a sterile holding tank. We add sterile liquid cryoprotectant solution to the centrifuged culture.

It is homogenized in the holding tank by the agitator. When homogenous, the culture is pumped into a sterile kettle (which is a functional aliquot for the cryofreezing or pelletizing of the product) to be pelletized in a liquid nitrogen vat. When complete the frozen pellets are lyophilized or freeze dried. After drying, we mill the freeze dried pellets into a fine powder. We will take the ground culture and homogenize it to ensure uniformity prior to sampling the culture for the quality assurance tests by morphological, physiological, 16S rRNA DNA sequences, and high temperature stress assays. Product is removed from the blender that was used to homogenize the material and then bag and store it at cool area, room temperatures.

Example 7—Formulation and Testing of *Pediococcus acidilactici* NRRL B-50517 in Food As knowledge of the health benefits of probiotics spreads and the demand for probiotic-infused food products continues to rise, food corporations are faced with a new set of challenges as they begin to collaborate with biotechnology companies. First, they must select one or more probiotic strains from the plethora of available options. Ideally, the chosen bacteria would need to: 1. Survive any manufacturing stress such as high heat treatment, 2. Possess compatibility with the chemical and physical properties of the desired food matrix, 3. Maintain viability in the food for the duration of the product's shelf life once incorporated, and 4. Resist destruction by digestive mechanisms in order to confer its health benefits to the host. Many probiotic strains popular in commercial supplements (such as *Lactobacillus* and *Bifidobacterium*) do not effectively fulfill these requirements and are thus unsuitable for industrial food production. Lacking the critical high heat resistance necessary to survive in recently pasteurized food, the applications of the two lactic acid bacteria (LAB) are severely limited in this context. The instability of these strains at room temperature would present additional complications in transport and storage for both food retailers and potential consumers. As facultative anaerobes to obligate anaerobes, *Lactobacillus* and *Bifidobacterium* would be especially vulnerable to losses in viability upon any exposure to oxygen, further reducing their potential for incorporation to food products. A more versatile, reliable strain is required to formulate effective probiotic-infused food.

*Pediococcus acidilactici* NRRL B-50517 is a uniquely formulated powder composed of the strain of bacteria capable of withstanding great variation in temperature, osmotic pressure, and oxygen exposure. A durable microorganism originally isolated from plant material, the probiotic has proven ability to survive in a wide range of food products under varying environmental conditions and heat treatment procedures.

Survival of *P. acidilactici* NRRL B-50517 in sucrose solutions ranging in concentration from 10 to 50% is indicative of probiotic resistance to osmotic pressure (Table 3). Where weaker bacteria would likely lose viability in a solution with comparably high osmolality, *P. acidilactici* NRRL B-50517 retains remarkably steady cell counts even at the highest tested concentration. Comparable results were obtained in solutions of lactose within the same concentration range over the course of 9 days (Table 4). In solutions of sterile water, 0.1 to 20% NaCl, and combined solutions of NaCl and sucrose, *P. acidilactici* NRRL B-50517 maintained significant cell viability in all assayed samples for up to one week, showcasing probiotic ability to adapt to a myriad of chemical environments (Table 5).

TABLE 3

Survival of *P. acidilactici* NRRL B-50517 incubated in high concentrated sucrose solution stored at room temperature
Numbers of *P. acidilactici* NRRL B-50517 viable cells after different incubation time in sucrose solution at room temperature

| % Sucrose solution | Control | 1 day | 3 days |
|---|---|---|---|
| 10% | 3.00E+08 | 5.20E+09 | N/A |
| 20% | 3.50E+08 | 3.00E+08 | 1.40E+08 |
| 30% | 3.30E+08 | 2.10E+08 | 1.50E+08 |

TABLE 3-continued

Survival of *P. acidilactici* NRRL B-50517 incubated in high concentrated sucrose solution stored at room temperature
Numbers of *P. acidilactici* NRRL B-50517 viable cells after different incubation time in sucrose solution at room temperature

| % Sucrose solution | Control | 1 day | 3 days |
|---|---|---|---|
| 40% | 5.10E+08 | 3.70E+08 | 3.10E+08 |
| 50% | 6.50E+08 | 4.70E+08 | 3.30E+08 |

*: 0.2 g 1Billion (1B) CFU/g *P. acidilactici* NRRL B-50517 was added to 20 mL of each sucrose solution and stored at room temperature. Viability tests were conducted by serially diluting sucrose + *P. acidilactici* NRRL B-50517 solution in 0.1% saline, plating onto MRS, and enumerating plates after overnight incubation.

**plates were contaminated on the third day, preventing continued testing for stability.

Conclusions: *P. acidilactici* NRRL B-50517 maintains viability in sucrose solutions ranging in concentration from 10-50%, indicating resistance of *P. acidilactici* NRRL B-50517 to high osmotic pressure environment

TABLE 4

Survival of *P. acidilactici* NRRL B-50517 incubated in high concentrated lactose solution stored at room temperature
Numbers of *P. acidilactici* NRRL B-50517 viable cells after different incubation time in lactose solution at room temperature

| % Lactose | Control | 1 day | 3 days | 7 days | 9 days |
|---|---|---|---|---|---|
| 10% | 1.20E+08 | 2.10E+08 | 1.90E+08 | 2.00E+08 | 8.00E+07 |
| 20% | 1.80E+08 | 1.40E+08 | 2.40E+08 | 2.10E+08 | 2.00E+08 |
| 30% | 2.30E+08 | 1.60E+08 | 4.30E+08 | 2.00E+08 | 1.60E+08 |
| 40% | 4.90E+08 | 3.70E+08 | 3.30E+08 | 3.67E+09 | 4.00E+08 |
| 50% | 1.80E+08 | 7.00E+07 | 1.00E+08 | 1.00E+09 | 1.50E+08 |

*: 0.2 g 1B/g *P. acidilactici* NRRL B-50517 was added to 20 mL of each lactose solution and stored at room temperature. Viability tests were conducted by serially diluting sucrose + *P. acidilactici* NRRL B-50517 solution in 0.1% saline, plating onto MRS, and enumerating plates after overnight incubation.

Conclusions: Over a period of 9 days, *P. acidilactici* NRRL B-50517 retained highly stable viable cell counts in 10% to 50% lactose solutions.

TABLE 5

Survival of *P. acidilactici* NRRL B-50517 incubated in high salt solution stored at room temperature
Numbers of *P. acidilactici* NRRL B-50517 viable cells after different incubation time in salt solution at room temperature

| Solution | 5 min | 30 min | 120 min | 7 days | 14 days | 22 days | 35 days |
|---|---|---|---|---|---|---|---|
| Sterile H2O only | 4.13E+08 | 4.31E+08 | 4.03E+08 | 1.01E+08 | 4.90E+05 | 0.00E+00 | 0.00E+00 |
| 0.1% NaCl | 3.88E+08 | 3.82E+08 | 3.72E+08 | 1.82E+08 | 9.80E+07 | 1.60E+07 | 1.10E+05 |
| 1% NaCl | 4.38E+08 | 3.98E+08 | 3.51E+08 | 1.82E+08 | 2.90E+07 | 9.00E+04 | 5.00E+03 |
| 2.5% NaCl | 4.98E+08 | 3.87E+08 | 4.02E+08 | 2.21E+08 | 5.70E+07 | 1.00E+04 | 0.00E+00 |
| 5% NaCl | 4.85E+08 | 3.40E+08 | 3.87E+08 | 1.39E+08 | 1.25E+08 | 2.90E+07 | 1.01E+06 |
| 7.5% NaCl | 3.82E+08 | 3.72E+08 | 4.60E+08 | 6.70E+07 | 4.20E+07 | 2.90E+07 | 7.12E+06 |
| 10% NaCl | 4.32E+08 | 4.08E+08 | 4.96E+08 | 4.70E+07 | 7.00E+06 | 3.00E+06 | 2.60E+05 |
| 20% NaCl | 4.53E+08 | 3.62E+08 | 5.36E+08 | 1.03E+08 | 5.10E+07 | 3.20E+07 | 4.52E+06 |
| 25% Sucrose, 10% NaCl | 3.92E+08 | 3.68E+08 | 4.80E+08 | 9.00E+07 | 5.60E+07 | 9.00E+06 | 1.56E+06 |

*: 0.2 g 1 B/g *P. acidilactici* NRRL B-50517 was added to 20 mL of different concentrations of NaCl or sucrose + NaCl solution and stored at room temperature. Viability tests were conducted by serially diluting NaCl + *P. acidilactici* NRRL B-50517 solution in 0.1% saline, plating onto MRS, and enumerating plates after overnight incubation.

When assayed extensively for viability, 5051® retained viable cell counts (CFU/g) for up to 113 days after incorporation to peanut butter when stored at room temperature, indicating high shelf stability (Table 6). The probiotic showed similarly successful results when heated to 85° C. in peanut butter with storage at room temperature thereafter. Stability was similarly constant when the probiotic was incorporated to 85° C.-heated pudding; cell counts remained within one log over a period of 29 days with refrigerator storage (Table 7).

TABLE 6

Integration of Pediococcus *acidilactici* NRRL B-50517 into commercial peanut butter
Numbers of viable cells after integrated *P. acidilactici* NRRL B-50517 into peanut butter stored at different temperature

| Days of storage | Room temperature | % Survival | 37° C. | % Survival |
|---|---|---|---|---|
| Control | 3.15E+10 | 100.00 | 3.15E+10 | 100.00 |
| 0 | 2.78E+10 | 88.18 | n/a | n/a |
| 7 | 1.34E+10 | 42.68 | 1.63E+10 | 51.85 |
| 14 | 2.33E+10 | 74.07 | 1.78E+10 | 56.44 |
| 22 | 2.91E+10 | 92.24 | 1.49E+10 | 47.27 |
| 113 | 4.78E+09 | 15.17 | 2.00E+07 | 0.06 |

*: Samples of *P. acidilactici* NRRL B-50517 and peanut butter were prepared by mixing 6 g of 100 B/g *P. acidilactici* NRRL B-50517 powder with 20 g peanut butter, then stored at either room temperature (23° C.) or 37° C. Stability tests were conducted by adding 0.1 g of the mixture to 5 mL 0.1% saline, serially diluting the solution for plating onto MRS, and enumerating plates after overnight incubation at 45° C. Percent survival was calculated as a fraction of a *P. acidilactici* NRRL B-50517 + saline control (0.2 g 100 B/g *P. acidilactici* NRRL B-50517 added to 10 mL 0.1% saline at room temperature).

Conclusion: *P. acidilactici* NRRL B-50517 shows high cell counts (CFU/g) in peanut butter at room temperature over a period of 113 days, indicating that a product containing both ingredients would maintain high shelf stability. Even when stored at 37° C., the peanut butter and *P. acidilactici* NRRL B-50517 mixture displays similarly high viability over 22 days, dropping off between the 22 and 113 day viability tests.

TABLE 7

Survival of *P. acidilactici* NRRL B-50517 in peanut butter after high
temperature (85° C.) treatment
Numbers of viable cells after heat treated integrated *P. acidilactici*
NRRL B-50517 into peanut butter at 85° C. and stored at room
temperature

| Peanut Butter | Day 1 | % Survival | Day 7 | % Survival | Day 14 | % Survival |
|---|---|---|---|---|---|---|
| Control | 3.15E+10 | 100.00 | 3.15E+10 | 100.00 | 3.15E+10 | 100.00 |
| PB 1 | 7.98E+09 | 25.33 | 1.01E+09 | 3.22 | 2.22E+09 | 7.04 |
| PB 2 | 1.38E+10 | 43.83 | 3.17E+09 | 10.05 | 3.67E+09 | 11.66 |
| Hazelnut | 2.53E+08 | 0.80 | 7.66E+08 | 2.43 | 8.11E+08 | 2.57 |

*: Samples of *P. acidilactici* NRRL B-50517 and peanut butter were prepared by mixing 1.2 g of 100 B/g *P. acidilactici* NRRL B-50517 powder into 3.8 g peanut butter. Empty tubes were heated to 85° C. before 0.5 g peanut butter and *P. acidilactici* NRRL B-50517 mixture was added and left on the hot plate for 5 min. After a 10 min cooling period, 10 mL 0.1% saline was added to each tube. Viability tests were conducted by serially diluting into saline, plating onto MRS, and enumerating plates after overnight incubation at 45° C. Percent survival was calculated as a fraction of a *P. acidilactici* NRRL B-50517 + saline control (0.2 g 100 B/g *P. acidilactici* NRRL B-50517 added to 10 mL 0.1% saline at room temperature).

Conclusion: Over a period of two weeks after high heat treatment, *P. acidilactici* NRRL B-50517 maintained high viability in nut butters, supporting compatibility of the *P. acidilactici* NRRL B-50517 with commercially produced nut products.

PB1 ingredients: roasted peanuts, sugar, hydrogenated vegetable oil (cottonseed, soybean, and rapeseed oil) to prevent separation, salt.

Hazelnut Spread ingredients: sugar, vegetable oil (palm and rapeseed oil), hazelnuts, cocoa powder, skim milk, whey, lactose, sunflower lecithin (emulsifier), natural vanilla flavor.

Testing of *P. acidilactici* NRRL B-50517 in five types of high-heat treated oil (corn oil, EVOO, LTOO, peanut oil, and vegetable oil) produced results analogous to those observed in peanut butter. Two of the oils, EVOO and corn oil (Table 8), displayed impressive survival rates even after 30 minutes of continuous exposure to 85° C. (Table 9 and Table 10). The apparent durability of the probiotic in oil is particularly conducive to its use in traditional food preparation techniques which involve heat.

TABLE 8

Survival of *P. acidilactici* NRRL B-50517 in commercial oil after high
temperature (85° C.) treatment
Numbers of viable cells after heat treated the integrated *P. acidilactici*
NRRL B-50517 into different types of oils

| Oil Type | Room | % Survival | Up to 85° C. | % Survival | 5 min at 85° C. | % Survival |
|---|---|---|---|---|---|---|
| Control | 2.75E+08 | 100.00 | 2.75E+08 | 100.00 | 2.75E+08 | 100.00 |
| Corn Oil | 6.75E+07 | 24.52 | 4.55E+07 | 16.53 | 6.00E+06 | 2.18 |
| EVOO | 9.70E+07 | 35.23 | 4.20E+07 | 15.25 | 1.10E+07 | 4.00 |
| LTOO | 5.90E+07 | 21.43 | 3.60E+07 | 13.08 | 5.30E+07 | 19.25 |
| Peanut Oil | 1.68E+08 | 61.02 | 2.30E+07 | 8.35 | 0.00E+00 | 0.00 |
| Vegetable Oil | 1.06E+08 | 38.50 | 4.70E+07 | 17.07 | 6.00E+06 | 2.18 |

*: 900 uL oil was heated to 85° C. on a hot plate before 0.1 g 1 B/g *P. acidilactici* NRRL B-50517 was added, then left for the specified period of time. Tubes were then removed and allowed to cool for a minimum of 10 min before serially diluting in 0.1% saline and plating on MRS. Plates were incubated overnight at 45° C. and enumerated the next day. Percent survival was calculated as a fraction of a saline + *P. acidilactici* NRRL B-50517 control (0.2 g 1 B/g *P. acidilactici* NRRL B-50517 added to 20 mL 0.1% saline at room temperature).

Conclusion: *P. acidilactici* NRRL B-50517 maintains high viable cell counts (CFU/g) in a variety of commercial oils at room temperature and after high temperature treatment.

TABLE 9

Effects on survival of *P. acidilactici* NRRL B-50517 in Olive oil after high temperature (85° C.) treatment at different time

| EVOO at different temperature | Numbers of viable cells after heat treated in integrated *P. acidilactici* NRRL B-50517 into olive oil | % Survival |
| --- | --- | --- |
| Room | 1.18E+08 | 100.00 |
| Up to 85° C. | 7.80E+07 | 66.10 |
| 85° C., 5 min | 1.90E+07 | 16.10 |
| 85° C., 15 min | 3.00E+05 | 0.25 |
| 85° C., 30 min | 2.00E+05 | 0.17 |

*: 900 uL oil was heated to 85 C. on a hot plate before 0.1 g *P. acidilactici* NRRL B- 50517 was added, then left for the specified period of time. Tubes were removed from the heat source and allowed to cool for a minimum of 10 min before serially diluted and plated onto MRS. Plates were incubated overnight at 45° C. and enumerated the next day. Percent survival at each length of heat treatment was calculated as a fraction of survival in EVOO at room temperature.

Conclusion: *P. acidilactici* NRRL B-50517 survives high heat treatment in EVOO, producing high viable cell numbers even after 30 min at 85° C. The probiotic would likely be compatible for a variety of food preparation techniques, including those involving heating.

TABLE 10

Effects on survival of *P. acidilactici* NRRL B-50517 in corn oil after high temperature (85° C.) treatment at different time

| Corn Oil Temperature | Numbers of viable cells after heat treated the integrated *P. acidilactici* NRRL B-50517 into corn oil | % Survival |
| --- | --- | --- |
| Room | 6.50E+07 | 100.00 |
| Up to 85° C. | 6.30E+07 | 96.92 |
| 85° C., 5 min | 4.00E+06 | 6.15 |
| 85° C., 15 min | 5.30E+05 | 0.82 |
| 85° C., 30 min | 3.00E+04 | 0.05 |

*: 900 uL oil was heated to 85 C. on a hot plate before 0.1 g *P. acidilactici* NRRL B- 50517 was added, then left for the specified period of time. Tubes were removed from the heat source and allowed to cool for a minimum of 10 min before serially diluted and plated onto MRS. Plates were incubated overnight at 37° C. and enumerated the next day. Percent survival at each length of heat treatment was calculated as a fraction of survival in corn oil at room temperature.

Conclusions: *P. acidilactici* NRRL B-50517 survives high heat treatment in corn oil, producing high viable cell numbers even after 30 min at 85° C. The probiotic would likely be compatible with a variety of food preparation techniques, including those involving heating.

*P. acidilactici* NRRL B-50517 can survive after 85° C. heat treated different food products dispenses into the different containers with *P. acidilactici* NRRL B-50517 simulated sterilization procedures used in the food industry (Table 11 and Table 12), and retain viability in products with diverse physiochemical properties for weeks or months. This provides a novel approach to introduce viable probiotics into foods.

TABLE 11

Survival of *P. acidilactici* NRRL B-50517 in pudding after high temperature (85° C.) treatment
Numbers of viable cells after heat treated the integrated *P. acidilactici* NRRL B-50517 into different types of pudding

| Days after 85° C. Treatment | Vanilla pudding | Chocolate pudding |
| --- | --- | --- |
| 1 | 3.55E+07 | 4.70E+07 |
| 2 | 6.90E+07 | 2.65E+07 |
| 3 | 6.05E+07 | 5.10E+07 |
| 6 | 3.60E+07 | 1.93E+07 |
| 14 | 3.55E+07 | 7.75E+06 |
| 29 | 6.10E+07 | 4.00E+06 |

*: A 100 mL cup of Shiny Spoon Pudding was emptied into two 50 mL tubes and heated to 85° C. for 20 min. The original container was cleaned with soap and water, dried, and filled with 2 g 10 B/g *P. acidilactici* NRRL B-50517. The heated pudding was then poured back into the original container, cooled for 20 min, then stored in the refrigerator overnight. The next day the pudding was mixed and assayed for viability by first diluting 2 g pudding in 5 mL saline, then serially diluting for plating onto MRS. Plates were incubated overnight and enumerated the following day.

Conclusion: After incorporation to either vanilla or chocolate pudding heated to 85° C. in conditions similar to pasteurization, *P. acidilactici* NRRL B-50517 maintains highly stable cell counts for approximately one month when stored at refrigerator temperature.

TABLE 12

Survival of *P. acidilactici* NRRL B-50517 in commercial food products after high temperature (85° C.) treatment

| | *P. acidilactici* NRRL B-50517 Survival After 85° C. Treatment | |
| --- | --- | --- |
| Food Product | CFU/g | % Survival |
| Control | 2.75E+08 | 100 |
| Ketchup | 9.83E+07 | 35.68 |
| Fruit Cup | 8.19E+07 | 29.75 |
| EVOO | 7.55E+07 | 27.42 |
| Great Value Oil | 2.43E+07 | 8.81 |
| 2.5% Lactose | 2.33E+07 | 8.46 |
| Strawberries in Syrup | 1.40E+07 | 5.09 |
| Orange Juice | 1.04E+07 | 3.79 |

*: Samples were prepared as follows:
1. 10 mL ketchup was heated at 85° C. for 20 min, then mixed with 0.4 g of 1 B/g *P. acidilactici* NRRL B-50517 and 5 mL sterile water and allowed to cool for 20 min before testing for viability.
2. 100 g fruit cup mixture was heated at 85° C. for 45 min, then poured back into the original container over 1 g 1 B/g *P. acidilactici* NRRL B-50517 and tested for viability.
3. Tubes of 5 mL EVOO and Great Value oil were heated at 85 C. for 20 min, then added to 0.2 g 1 B/g *P. acidilactici* NRRL B-50517 and tested for viability.
4. A tube containing 5 mL 2.5% lactose was heated at 85° C. for 20 min, then added to a 15 mL tube containing 0.2 g 1 B/g *P. acidilactici* NRRL B-50517. The tube was allowed to cool for 20 minutes before testing for viability.
5. 283 g strawberry in syrup mixture was poured into a beaker, heated at 85° C. for 30 min, then poured back into original container on top of 2 g 1 B/g *P. acidilactici* NRRL B-50517. After cooling for 20 min, the mixture was tested for viability.
6. 5 mL orange juice was heated to 85° C. for 20 min, then added to 0.1 g 1 B/g *P. acidilactici* NRRL B-50517, cooled for 20 min and tested for viability.
**All viability testing was conducted by serially diluting *P. acidilactici* NRRL B-50517 + heat-treated food mixture in 0.1% saline, plating onto MRS, and enumerating plates after overnight incubation. Percent survival was calculated as a fraction of a saline + *P. acidilactici* NRRL B-50517 control (0.2 g 1 B/g *P. acidilactici* NRRL B-50517 added to 20 mL 0.1% saline at room temperature).

Conclusion: *P. acidilactici* NRRL B-50517 maintains viability in a variety of liquid and solid matrices after high heat treatment, indicating high compatibility for incorporation to many different foods after pasteurization or other similar high- heat sterilization procedures.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A composition comprising an effective amount of *Pediococcus acidilactici* probiotic for use in a method of treating a disease or condition characterized by inflammation in a subject in need thereof, wherein the *Pediococcus acidilactici* probiotic is strain NRRL B-50517.

2. The composition of claim 1, wherein the *Pediococcus acidilactici* probiotic is formulated as a tablet.

3. The composition of claim 1, wherein the *Pediococcus acidilactici* probiotic is formulated as a capsule.

4. The composition of claim 3, comprising peach fruit powder as a flavorant.

5. A food product comprising the composition of claim 1.

6. The food product of claim 5, wherein the food comprises peanut butter.

7. The food product of claim 5, wherein the food comprises pudding.

8. The food product of claim 5, wherein the food comprises an oil.

9. The food product of claim 5, wherein the food comprises a beverage.

10. The food product of claim 9, wherein the beverage comprises fruit juice.

11. The food product of claim 5, wherein the food comprises ketchup.

12. The food product of claim 5, wherein the food comprises a fruit cup.

13. The food product of claim 5, wherein the food comprises strawberry syrup.

14. The food product of claim 5, wherein the food comprises milk.

\* \* \* \* \*